(12) United States Patent
Di Carlo et al.

(10) Patent No.: US 11,931,481 B2
(45) Date of Patent: **\*Mar. 19, 2024**

(54) MICROPOROUS ANNEALED PARTICLE GEL SYSTEM

(71) Applicant: THE REGENTS OF THE UNIVERSITY OF CALIFORNIA, Oakland, CA (US)

(72) Inventors: Dino Di Carlo, Los Angeles, CA (US); Westbrook Weaver, San Diego, CA (US); Tatiana Segura, Durham, NC (US); Jaekyung Koh, Los Angeles, CA (US); Philip Scumpia, Los Angeles, CA (US); Donald R. Griffin, Charlottesville, VA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/877,933

(22) Filed: Jul. 30, 2022

(65) Prior Publication Data
US 2022/0370686 A1    Nov. 24, 2022

Related U.S. Application Data

(62) Division of application No. 16/077,985, filed as application No. PCT/US2017/017837 on Feb. 14, 2017.

(60) Provisional application No. 62/295,933, filed on Feb. 16, 2016.

(51) Int. Cl.
*A61L 27/52* (2006.01)
*A61K 9/00* (2006.01)
(Continued)

(52) U.S. Cl.
CPC ............ *A61L 27/52* (2013.01); *A61K 9/0019* (2013.01); *A61K 9/1635* (2013.01);
(Continued)

(58) Field of Classification Search
None
See application file for complete search history.

(56) References Cited

U.S. PATENT DOCUMENTS

| 4,726,877 A | 2/1988 | Fryd et al. |
| 4,753,865 A | 6/1988 | Fryd et al. |

(Continued)

FOREIGN PATENT DOCUMENTS

| CN | 1543339 | 11/2004 |
| CN | 101410098 | 4/2009 |

(Continued)

OTHER PUBLICATIONS

Seliktar, et al., MMP-2 sensitive, VEGF-bearing bioactive hydrogels for promotion of vascular healing. J. Biomed. Mater. Res. A,68:704-716 (2004).

(Continued)

*Primary Examiner* — M Franco G Salvoza
(74) *Attorney, Agent, or Firm* — VISTA IP LAW GROUP LLP (57) ABSTRACT

A hydrogel material for use in a human subject or other mammal includes a collection of microgel particles having one or more network cross linker components, wherein the microgel particles, when exposed to an endogenous or exogenous annealing agent, links the microgel particles together in situ to form a covalently-stabilized scaffold of microgel particles having pores formed between the microgel particles wherein the pores are substantially devoid of hydrogel.

18 Claims, 4 Drawing Sheets

(51) Int. Cl.
 *A61K 9/16*    (2006.01)
 *A61K 39/39*   (2006.01)
 *A61L 27/54*   (2006.01)
 *A61L 27/56*   (2006.01)
 *C08H 1/00*   (2006.01)
 *A61K 39/00*   (2006.01)

(52) U.S. Cl.
 CPC .......... *A61K 9/1641* (2013.01); *A61K 9/1652* (2013.01); *A61K 39/39* (2013.01); *A61L 27/54* (2013.01); *A61L 27/56* (2013.01); *C08H 1/00* (2013.01); *A61K 2039/60* (2013.01); *A61K 2039/6093* (2013.01); *A61L 2300/426* (2013.01); *A61L 2300/64* (2013.01); *A61L 2400/06* (2013.01)

(56) References Cited

U.S. PATENT DOCUMENTS

| | | |
|---|---|---|
| 5,102,597 A | 4/1992 | Roe et al. |
| 5,124,188 A | 6/1992 | Roe et al. |
| 5,213,580 A | 5/1993 | Slepian et al. |
| 5,575,815 A | 11/1996 | Slepian et al. |
| 5,843,156 A | 12/1998 | Slepian et al. |
| 5,854,382 A | 12/1998 | Loomis |
| 6,005,020 A | 12/1999 | Loomis |
| 6,007,833 A | 12/1999 | Chudzik et al. |
| 6,028,164 A | 2/2000 | Loomis |
| 6,063,061 A | 5/2000 | Wallace et al. |
| 6,066,325 A | 5/2000 | Wallace et al. |
| 6,156,345 A | 12/2000 | Chudzik et al. |
| 6,290,729 B1 | 9/2001 | Slepian et al. |
| 6,316,522 B1 | 11/2001 | Loomis et al. |
| 6,403,758 B1 | 6/2002 | Loomis |
| 6,495,127 B1 | 12/2002 | Wallace et al. |
| 6,534,560 B2 | 3/2003 | Loomis et al. |
| 6,602,975 B2 | 8/2003 | Hubbell |
| 6,660,827 B2 | 12/2003 | Oomis et al. |
| 6,669,827 B2 | 12/2003 | Austin |
| 6,924,370 B2 | 8/2005 | Chudzik et al. |
| 6,946,499 B2 | 9/2005 | Loomis et al. |
| 7,094,418 B2 | 8/2006 | Chudzik et al. |
| 7,109,255 B2 | 9/2006 | Loomis et al. |
| 7,442,384 B2 | 10/2008 | Loomis et al. |
| 7,547,445 B2 | 6/2009 | Chudzik et al. |
| 7,615,373 B2 | 11/2009 | Simpson et al. |
| 7,687,530 B2 | 3/2010 | Williams |
| 7,776,063 B2 | 8/2010 | Sawhney et al. |
| 7,785,617 B2 | 8/2010 | Shakesheff |
| 7,964,217 B2 | 6/2011 | Harris |
| 8,318,193 B2 | 11/2012 | Ratner et al. |
| 8,357,378 B2 | 1/2013 | Wallace et al. |
| 8,557,288 B2 | 10/2013 | Elbert et al. |
| 8,603,511 B2 | 12/2013 | Wallace et al. |
| 8,927,022 B2 | 1/2015 | Maginness et al. |
| 9,234,171 B2 | 1/2016 | Lee et al. |
| 10,576,185 B2 | 3/2020 | Weaver et al. |
| 10,668,185 B2 | 6/2020 | Weaver et al. |
| 10,912,860 B2 | 2/2021 | Griffin et al. |
| 11,464,886 B2 | 10/2022 | Griffith et al. |
| 2002/0091229 A1 | 7/2002 | Hubbell |
| 2002/0176880 A1 | 11/2002 | Cruise et al. |
| 2004/0078004 A1 | 4/2004 | Bourne et al. |
| 2004/0241203 A1 | 12/2004 | Shakesheff et al. |
| 2004/0258731 A1 | 12/2004 | Shimoboji et al. |
| 2005/0119762 A1 | 6/2005 | Zilla et al. |
| 2006/0093639 A1 | 5/2006 | Starkebaum |
| 2006/0257485 A1 | 11/2006 | Kumacheva |
| 2007/0141105 A1 | 6/2007 | Stein et al. |
| 2007/0167541 A1 | 7/2007 | Ruberti et al. |
| 2008/0193536 A1 | 8/2008 | Khademhosseini |
| 2009/0011009 A1 | 1/2009 | Benita et al. |
| 2009/0294049 A1 | 12/2009 | Udipi et al. |
| 2009/0311324 A1 | 12/2009 | Steinfeld et al. |
| 2010/0036503 A1 | 2/2010 | Chen et al. |
| 2010/0068286 A1 | 3/2010 | Troiano et al. |
| 2010/0272805 A1 | 10/2010 | Singh et al. |
| 2011/0087152 A1 | 4/2011 | David et al. |
| 2011/0256628 A1 | 10/2011 | Galperin et al. |
| 2011/0257623 A1 | 10/2011 | Marshall et al. |
| 2012/0015440 A1 | 1/2012 | Otsuka et al. |
| 2012/0027775 A1 | 2/2012 | Won et al. |
| 2012/0114615 A1 | 5/2012 | Burdick et al. |
| 2012/0116511 A1 | 5/2012 | Borden |
| 2012/0134968 A1 | 5/2012 | Wang et al. |
| 2012/0156259 A1 | 6/2012 | Rau et al. |
| 2012/0202263 A1 | 8/2012 | Blakely et al. |
| 2012/0308508 A1 | 12/2012 | Saunders et al. |
| 2013/0143056 A1 | 6/2013 | Swan et al. |
| 2013/0228530 A1 | 9/2013 | Di Carlo et al. |
| 2013/0233420 A1 | 9/2013 | Di Carlo et al. |
| 2014/0112960 A1 | 4/2014 | Lin |
| 2014/0120078 A1 | 5/2014 | Wallace et al. |
| 2014/0178455 A1 | 6/2014 | Nukavarapu et al. |
| 2014/0228453 A1 | 8/2014 | Bennett et al. |
| 2014/0230909 A1 | 8/2014 | Di Carlo et al. |
| 2014/0315805 A1 | 10/2014 | Carmichael et al. |
| 2015/0071997 A1 | 3/2015 | Garcia et al. |
| 2015/0104427 A1 | 4/2015 | Segura |
| 2015/0202305 A1 | 7/2015 | Maynard et al. |
| 2015/0290362 A1 | 10/2015 | Douglas et al. |
| 2015/0359752 A1 | 12/2015 | Lu et al. |
| 2016/0116453 A1 | 4/2016 | Lutolf et al. |
| 2016/0279283 A1 | 9/2016 | Griffin et al. |
| 2016/0303281 A1 | 10/2016 | Salamone et al. |
| 2017/0368224 A1 | 12/2017 | Griffin et al. |
| 2018/0078671 A1 | 3/2018 | Griffin et al. |
| 2020/0085859 A1 | 3/2020 | Griffin |
| 2021/0138105 A1 | 5/2021 | Griffin et al. |

FOREIGN PATENT DOCUMENTS

| | | | |
|---|---|---|---|
| CN | 104582747 | 4/2015 | |
| EP | 1041970 A1 | 10/2000 | |
| EP | 1063975 A1 | 1/2001 | |
| EP | 1063975 B1 | 5/2005 | |
| EP | 2542620 A1 | 1/2013 | |
| EP | 1041970 31 | 7/2013 | |
| EP | 2542620 B1 | 6/2016 | |
| EP | 3169372 | 5/2017 | |
| GB | 2431104 | 4/2007 | |
| JP | 2004-523484 | 8/2004 | |
| WO | WO 95/09659 A1 | 4/1995 | |
| WO | WO 99/47129 A1 | 9/1999 | |
| WO | WO 00/24378 | 5/2000 | |
| WO | WO 02/40242 A1 | 5/2002 | |
| WO | WO 02/071994 | 9/2002 | |
| WO | WO 2014/025312 | 2/2004 | |
| WO | WO 2005/006101 A2 | 1/2005 | |
| WO | WO 2005/035735 A2 | 4/2005 | |
| WO | WO 2008/093095 A1 | 8/2008 | |
| WO | WO-2010017264 A2 * | 2/2010 | ............. A61K 47/34 |
| WO | WO-2010123938 A2 * | 10/2010 | ............ A61L 27/227 |
| WO | WO 00/24378 A1 | 8/2011 | |
| WO | WO 2011/101684 A1 | 8/2011 | |
| WO | WO 2012/155110 A1 | 11/2012 | |
| WO | WO 2013/071126 A1 | 5/2013 | |
| WO | WO 2014/142653 A1 | 9/2014 | |
| WO | WO 2016/011387 A1 | 1/2016 | |
| WO | WO 2016/096054 A1 | 6/2016 | |
| WO | WO 2017/127717 | 7/2017 | |
| WO | WO 2017/136427 | 8/2017 | |
| WO | WO 2017/142879 | 8/2017 | |
| WO | WO 2018/136205 | 7/2018 | |

OTHER PUBLICATIONS

Sokic, et al., In situ generation of cell-laden porous MMP-sensitive PEGDA hydrogels by gelatin leaching. Macromol. Biosci. 14:731-739 (2014).

Stachowiak, et al., Bioactive Hydrogels with an Ordered Cellular Structure Combine Interconnected Macroporosity and Robust Mechanical Properties. Adv. Mater. 17:399-403 (2005).

(56) References Cited

OTHER PUBLICATIONS

Stratman, et al., Pericyte recruitment during vasculogenic tube assembly stimulates endothelial basement membrane matrix formation. Blood 114:5091-5101 (2009).
Wade, R. J. and Burdick, J. A. Engineering ECM signals into biomaterials. Mater. Today 15:454-459 (2012).
Wang, et al. Multifunctional chondroitin sulphate for cartilage tissue-biomaterial integration. Nat. Mater.6:385-392 (2007).
Wang, H.-M. et al. Novel Biodegradable Porous Scaffold Applied to Skin Regeneration. PLOS ONE8:e56330 (2013).
Yang, et al., The Design of Scaffolds for Use in Tissue Engineering. Part I. Traditional Factors. Tissue Eng. 7:679-689 (2001).
Yeh, et al., Elastic modulus measurements of human liver and correlation with pathology. Ultrasound Med. Biol.28:467-474 (2002).
PCT International Preliminary Report on Patentability (Chapter I of the Patent Cooperation Treaty) for PCT/US2015/040962, Applicant: The Regents of the University of California, Form PCT/IB/326 and 373, dated Jan. 26, 2017 (18pages).
Du et al., Directed assembly of cell-laden microgels for fabrication of 3D tissue constructs, PNAS, vol. 105(28):9522-9527 (Jul. 15, 2008).
Ergenc et al., Recent Advances in the Modeling of PEG Hydrogel Membranes for Biomedical Applications, Biomedical Applications, Biomedical Engineering, Trends in Materials Science, Mr Anthony Laskovski (Ed.), ISBN: 978-953-307-513-6, Chapter 14, pp. 307-346 (2011).
Guan et al., PNIPAM microgels for biomedical applications: from dispersed particles to 3D assemblies, Soft Matter, vol. 7:6375-6384 (2011).
Jia et al., Hyaluronic Acid-Based Microgels and Microgel Networks for Vocal Fold Regeneration, Biomacromolecues, 2006, 7 (12), pp. 3336-3344.
Park et al., Bovine Primary Chondrocyte Culture in Synthetic Matrix Metallopreteinase-Sensitive Poly(ethylene glycol)-Based Hydrogels as a Scaffold for Cartillage Repair, Tissue Engineering, vol. 10(3/4/):515-522 (2004).
Sala et al., Microstructured Polymer Films and Matrices for Tissue Engineering, Poster Session, University of Zurich, Institute for Biomedical Engineering, 1 page with 2 pages of citation info, 2007, also available at http://www.lbb.ethz.ch/Publications/Posters/CCMXposter.pdf (last visited Dec. 21, 2016).
Thorne et al., Microgel applications and commercial considerations, Colloid. Polym. Sci., vol. 289:625-646 (2011).
Turturro et al., MMP-Sensitive PEG Diacrylate Hydrogels with Spatial Variations in Matrix Properties Stimulate Directional Vascular Sprout Formation, PLoS ONE 8(3): e58897. doi:10.1371/journal.pone.0058897, pp. 1-14 (Mar. 12, 2013).
Alijotas-Reig et al. Late-Onset Inflammatory Adverse Reactions Related to Soft Tissue Filler Injections. Clin. Rev. Allergy Immunol. 45:97-108 (Aug. 2013).
Conchouso et al. Three-dimensional parallelization of microfluidic droplet generators for a litre per hour volume production of single emulsions. Lab. Chip14: 3011-3020 (Aug. 2014).
Das et al. Biomaterials and Nanotherapeutics for Enhancing Skin Wound Healing. Front Bioeng Biotechnol 4:82 (Oct. 2016).
De France et al. Structured Macroporous Hydrogels: Progress, Challenges, and Opportunities. Adv Healthc Mater 7(1):17 pgs (Jan. 2018).
Du et al. Fabrication of Hexagonal-Prismatic Granular Hydrogel Sheets. Langmuir 34(11):3459-3466 (2018).
Grainger. Wound healing: Enzymatically crosslinked scaffolds. Nat Mater 14:662-663 (2015).
Griffin et al. Accelerated wound healing by injectable microporous gel scaffolds assembled from annealed building blocks. Nat Mater 14:737-744 (Jun. 2015).
Griffin et al. Hybrid photopatterned enzymatic reaction (HyPER) for in situ cell manipulation. Chembiochem Eur. J. Chem. Biol.15:233-242 (Jan. 2014).
Guvendiren et al. Engineering synthetic hydrogel microenvironments to instruct stem cells. CWT Opin Biotechnol 24:841-846 (Oct. 2013).
Hunckler et al. A current affair: electrotherapy in wound healing. J Multidiscip Healthc 10:179-194 (Apr. 2017).
Jgamadze et al. Thermoswitching Microgel Carriers Improve Neuronal Cell Growth and Cell Release for Cell Transplantation. Tissue Eng. Part C Methods (Jan. 2014).
Jiang et al. Cell-laden microfluidic microgels for tissue regeneration. Lab Chip 16(23):4482-4506 (Nov. 2016).
Lee et al. Tissue, cell and engineering. Curr. Opin. Biotechnol. 24:827-829 (Oct. 2013).
Ling et al. A cell-laden microfluidic hydrogel. Lab Chip 7(6):756-762 (Jun. 2007).
Muehleder et al. Connections matter: channeled hydrogels to improve vascularization. Front Bioeng Biotechnol 2:52 (Nov. 201).
Nih et al. Injection of Microporous Annealing Particle (MAP) Hydrogels in the Stroke Cavity Reduces Gliosis and Inflammation and Promotes NPC Migration to the Lesion. Adv Mater 29(32):1606471 (2017).
Qi et al. DNA-directed self-assembly of shape-controlled hydrogels. Nat. Commun. 4:2275 (2013).
Sokic et al. In situ generation of cell-laden porous MMP-sensitive PEGDA hydrogels by gelatin leaching. Macromol. Biosci. 14:731-739 (May 2014).
Stejskalova et al. Using biomaterials to rewire the process of wound repair. Biomater Sci 5(8):1421-1434 (Jul. 2017).
Wang et al. Novel Biodegradable Porous Scaffold Applied to Skin Regeneration. PLoS ONE8:e56330 (Jun. 2013).
Kin et al. Assembly of PEG Microgels into Porous Cell-Instructive 3D Scaffolds via Thiol-Ene Click Chemistry. Adv Healthc Mater 7(11):e1800160 (Jun. 2018).
Gan, Tiantian et al., In Situ Gelation of P(NIPAM-HEMA) Microgel Dispersion and Its Applications as Injectable 3D Cell Scaffold, Biomacromolecules 2009, 10, 1410-1415.
Guan, Ying et al., PNIPAM microgels for biomedical applications: from dispersed particles to 3D assemblies, Soft Matter, 2011, 7, 6375-6384.
Hu, Zhibing et al., Hydrogel Nanoparticle Dispersions with Inverse Thermoreversible Gelation, Adv. Mater. 2004, 16, No. 4, Feb. 17, 305-309, DOI: 10.1002/adma.200305560.
Karg, Matthias et al., New "smart" poly(NIPAM) microgels and nanoparticle microgel hybrids: Properties and advances in characterisation, Current Opinion in Colloid & Interface Science 14 (2009) 438-450.
Saunders, Brian R. et al., Microgel particles as model colloids: theory, properties and applications, Advances in Colloid and Interface Science, 80 (1999) 1-25.
Yin, Yadong et al., Self-Assembly of Monodispersed Spherical Colloids into Complex Aggregates with Well-Defined Sizes, Shapes, and Structures, Adv. Mater. 2001, 13, No. 4, Feb. 19, 267-271.
Zhou, Jun et al., Viscoelastic Behavior and In Vivo Release Study of Microgel Dispersions with Inverse Thermoreversible Gelation, Biomacromolecules 2008, 9, 142-148.
PCT International Search Report for PCT/US2015/040962, Applicant: The Regents of the University of California, Form PCT/ISA/210 and 220, dated Oct. 7, 2017 (6 pages).
PCT Written Opinion of the International Search Authority for PCT/US2015/040962, Applicant: The Regents of the University of California, Form PCT/ISA/237, dated Oct. 7, 2017 (16 pages).
Cha, Chaenyung et al., Microfluidics-Assisted Fabrication of Gelatin-Silica Core-Shell Microgels for Injectable Tissue Constructs, dx.doi.org/10.1021/bm401533y, Biomacromolecules 2014, 15, 283-290.
Du, Yanan et al., Directed assembly of cell-laden microgels for fabrication of 3D tissue constructs, 9522-9527, PNAS, Jul. 15, 2008, vol. 105, No. 17.
Office Action dated Oct. 3, 2022 for U.S. Appl. No. 16/071,252, Inventor: Dino Di Carlo, (87 pages).
Xian Xu et al., Hyaluronic Acid-Based Hydrogels: from a Natural Polysaccharide to Complex Networks, Soft Matter. 2012; 8(12): 3280-3294. Doi:10.1039/C2SM06463D.

(56) References Cited

OTHER PUBLICATIONS

Gaulding, Jeffrey C. et al., Reversible Inter- and Intra-Microgel Cross-Linking Using Disulfides, Macromolecules, 2012, vol. 45, pp. 39-45.
Syrett, Jay A. et al., Functional, star polymeric molecular carriers, built from biodegradable microgel/nanogel cores, Chem. Commu., 2011, vol. 47, pp. 1449-1451.
Response to Notice of Rejection dated Jul. 2, 2019 in Japanese Patent Application No. 2017-502712, (12 pages).
Request for Continued Examination dated Feb. 7, 2019 in U.S. Appl. No. 15/829,440, (31 pages).
Examination—Response to an Examiner's Report dated Nov. 21, 2019 in Australian Patent Appl No. 2015289474, (10pages).
Notice of Acceptance dated Nov. 26, 2019 in Australian Patent Appl No. 2015289474, (3pages).
Response to Office Action dated Nov. 22, 2019 in Brazilian Patent Appl No. 112017000813-0, (17pages).
Office Action dated Nov. 18, 2019 in U.S. Appl. No. 16/596,312, (13pages).
Amendment and Response to Office Action dated Dec. 9, 2019 in U.S. Appl. No. 16/596,312, (9pages).
Restriction Requirement dated Jan. 23, 2020 in U.S. Appl. No. 16/596,312, (10pages).
Notice of Allowance dated Dec. 24, 2019 in Japanese Patent Application No. 2017-502712, (4pages).
Notification of Defects dated Mar. 24, 2020 in Israel Patent Application No. 250092, (7pages).
Notification of Defects dated Aug. 6, 2020 for Israel Patent Application No. 250092, (7pages).
Notice of Issuance dated Jun. 4, 2020 for Chinese Patent Application No. 2015800494786, (4pages).
Office Action including partial translation dated Sep. 24, 2020 for Brazilian Patent Appl No. 112017000813-0, (6pages).
Communication pursuant to Article 94(3) EPC dated Oct. 7, 2020 for European Patent Appl No. 15821310.8-1109 (10pages).
Chan et al.: Functionalizable hydrogel microparticles of tunable size and stiffness for soft-tissue filler applications. Acta Biomaterialia 10:2563-3573 (2014).
Hao et al.: Visible light cured thiol-vinyl hydrogels with tunable degradation for 3D cell culture. Acta Biomater 10:1-27 (2014).
Quinn et al.: Biocompatible, glucose-permeable hydrogel for in situ coating of implantable biosensors. Biomaterials 18:1665-1670 (1997).
Rolfe et al.: The Fibrotic Response to Implanted Biomaterials: Implications for Tissue Engineering. Regenerative Medicine and Tissue Engineering—Cells and Biomaterials 26:551-570 (2011).
Tous et al.: Injectable Acellular Hydrogels for Cardiac Repair. J. of Cardiovasc. Trans. Res. 4:528-542 (2011).
Yadong et al.: Self-Assembly of Monodispersed Spherical Colloids into Complex Aggregates with Well-Defined Sizes, Shapes, and Structures; Adv. Mater., 13/4; 267-271 (2001).
PCT International Search Report for PCT/US2017/017837, Applicant: The Regents of the University of California, Form PCT/ISA/210 and 220, dated Apr. 25, 2017 (5pages).
PCT Written Opinion of the International Search Authority for PCT/US2017/017837, Applicant: The Regents of the University of California, Form PCT/ISA/237, dated Apr. 25, 2017 (9pages).
Bala, Indu et al., PLGA Nanoparticles in Drug Delivery: The State of the Art, Critical Review TM in Therapeutic Drug Carrier Systems, 21(5):387-422(2004).
Griffin, Donald R. et al., Accelerated wound healing by injectable microporous gel scaffolds assembled from annealed building blocks, Nature Materials, Advance Online Publication, www.nature.com/naturematerials, publised online: Jun. 1, 2015, DOI:10.1038/NMAT4294 (8pages).
Griffin, Donald R. et al., Photodegradable macromers and hydrogels for live cell encapsulation and release, J Am Chem Soc. Aug. 8, 2012; 134(31):13103-13107. doi:10.1021/ja305280w.
Shin, Dong-Sik et al., Photodegradable Hydrogels for Capture, Detection, and Release of Live Cells, Angew Chem Int Ed Engl. Jul. 28, 2014; 53(31):8221-8224, doi:10.1002/anie.201404323.

Yanagawa, Fumiki et al., Partially photodegradable hybrid hydrogels with elasticity tunable by light irradiation, Colloids and Surfaces B: Biointerfaces 126 (2015) 575-579.
PCT International Preliminary Report on Patentability (Chapter I of the Patent Cooperation Treaty) for PCT/US2017/017837, Applicant: The Regents of the University of California, Form PCT/IB/326 and 373, dated Aug. 30, 2018 (11pages).
Alijotas-Reig, et al., Late-Onset Inflammatory Adverse Reactions Related to Soft Tissue Filler Injections. Clin. Rev. Allergy Immunol. 45: 97-108 (2013).
Anna, et al., Formation of dispersions using 'flow focusing' in microchannels. Appl. Phys. Lett.82:364-366 (2003).
Bramfeld, et al., Scaffold Vascularization: A Challenge for Three-Dimensional Tissue Engineering. Curr. Med. Chem.17:3944-3967 (2010).
Burdick, et al., Controlled Degradation and Mechanical Behavior of Photopolymerized Hyaluronic Acid Networks. Biomacromolecules 6:386-391 (2005).
Chen, et al., Young's modulus measurements of soft tissues with application to elasticity imaging. IEEE Trans. Ultrason. Ferroelectr. Freq. Control43:191-194 (1996).
Chen, H.et al. Hydrogel-thickened microemulsion for topical administration of drug molecule at an extremely low concentration. Int. J. Pharm.341, 78-84 (2007).
Cheng, S. and Bilston, L. E. Unconfined compression of white matter. J. Biomech.40:117-124 (2007).
Conchouso, et al., Three-dimensional parallelization of microfluidic droplet generators for a litre per hour volume production of single emulsions. Lab. Chip14: 3011-3020 (2014).
Discher, et al. Growth Factors, Matrices, and Forces Combine and Control Stem Cells. Science324:1673-1677 (2009).
Du, et al., Directed assembly of cell-laden microgels for fabrication of 3D tissue constructs. Proc. Natl. Acad. Sci. 105:9522-9527 (2008).
Dunne, et al., Influence of particle size and dissolution conditions on the degradation properties of polylactide-co-glycolide particles. Biomaterials21:1659-1668 (2000).
Fukano, Y.et al. Characterization of an in vitro model for evaluating the interface between skin and percutaneous biomaterials. Wound Repair Regen 14: 484-491 (2006).
Fukano, Y.et al. Epidermal and dermal integration into sphere-templated porous poly(2-hydroxyethyl methacrylate) implants in mice.J. Biomed. Mater. Res. A94A:1172-1186 (2010).
Galiano, et al., Quantitative and reproducible murine model of excisional wound healing. Wound Repair Regen. Off. Publ. Wound Heal. Soc. Eur. Tissue Repair Soc. 12: 485-492 (2004).
Galler, et al., Self-Assembling Multidomain Peptide Hydrogels: Designed Susceptibility to Enzymatic Cleavage Allows Enhanced Cell Migration and Spreading. J. Am. Chem. Soc. 132: 3217-3223 (2010).
Garstecki, et al., Formation of droplets and bubbles in a microfluidic T-junction-scaling and mechanism of break-up. Lab. Chip 6:437-446 (2006).
Gorgieva, S. and Kokol, V. Preparation, characterization, and in vitro enzymatic degradation of chitosan-gelatine hydrogel scaffolds as potential biomaterials. J. Biomed. Mater. Res. A 100:1655-1667 (2012).
Griffin, et al. Hybrid photopatterned enzymatic reaction (HyPER) for in situ cell manipulation. Chembiochem Eur. J. Chem. Biol. 15:233-242 (2014).
Guvendiren, M. & Burdick, J. A. Engineering synthetic hydrogel microenvironments to instruct stem cells. Curr. Opin. Biotechnol. 24:841-846 (2013).
Hollister, S. J. Porous scaffold design for tissue engineering. Nat. Mater.4:518-524 (2005).
Hosokawa, et al., Handling of Picoliter Liquid Samples in a Poly(dimethylsiloxane)-Based Microfluidic Device. Anal. Chem 71: 4781-4785 (1999).
Huebsch, N.et al. Harnessing traction-mediated manipulation of the cell/matrix interface to control stem-cell fate. Nat. Mater.9: 518-526 (2010).

(56) References Cited

OTHER PUBLICATIONS

Jgamadze, et al. Colloids as mobile substrates for the implantation and integration of differentiated neurons into the mammalian brain. PloS One7, e30293 (2012).

Jgamadze, et al., Thermoswitching Microgel Carriers Improve Neuronal Cell Growth and Cell Release for Cell Transplantation. Tissue Eng. Part C Methods (2014). doi:10.1089/ten.TEC.2013.0752.

Kawakatsu, et al., Regular-sized cell creation in microchannel emulsification by visual microprocessing method. J. Am. Oil Chem. Soc.74:317-321 (1997).

Kong, et al., Controlling rigidity and degradation of alginate hydrogels via molecular weight distribution. Biomacromolecules 5:1720-1727 (2004).

Lee, K. and Hubbell, J. A. Tissue, cell and engineering. Curr. Opin. Biotechnol. 24:827-829 (2013).

Li, et al., DNA-templated assembly of droplet-derived PEG microtissues. Lab. Chip11:2967-2975 (2011).

Lin, et al., Eph/ephrin signaling in epidermal differentiation and disease. Semin. Cell Dev. Biol.23:92-101 (2012).

Lucas, T.et al. Differential Roles of Macrophages in Diverse Phases of Skin Repair.J. Immunol. 184:3964-3977 (2010).

Lutolf, M. P. and Hubbell, J. A. Synthetic biomaterials as instructive extracellular microenvironments for morphogenesis in tissue engineering. Nat. Biotechnol.23:47-55 (2005).

Lutolf, M. P.et al. Synthetic matrix metalloproteinase-sensitive hydrogels for the conduction of tissue regeneration: Engineering cell-invasion characteristics. Proc. Natl. Acad. Sci. 100: 5413-5418 (2003).

Madden, L. R.et al. Proangiogenic scaffolds as functional templates for cardiac tissue engineering. Proc. Natl. Acad. Sci. 107:15211-15216 (2010).

Parker, et al., Tissue response to mechanical vibrations for 'sonoelasticity imaging'. Ultrasound Med. Biol. 16:241-246 (1990).

Pautot, et al., Colloid-guided assembly of oriented 3D neuronal networks. Nat. Methods5: 735-740 (2008).

PCT/US2015/040962 International Search Report and Written Opinion dated Oct. 7, 2015.

Peters, et al., Engineering vascular networks in porous polymer matrices. J. Biomed. Mater. Res.60:668-678 (2002).

Qi, H.et al. DNA-directed self-assembly of shape-controlled hydrogels. Nat. Commun.4, (2013).

Richardson, et al., Polymeric system for dual growth factor delivery. Nat. Biotechnol. 19:1029-1034 (2001).

Rustad, K. C.et al. Enhancement of mesenchymal stem cell angiogenic capacity and stemness by a biomimetic hydrogel scaffold. Biomaterials 33:80-90 (2012).

Samani, et al., Measuring the elastic modulus of ex vivo small tissue samples. Phys. Med. Biol.48: 2183 (2003).

Schense, et al., Cross-linking exogenous bifunctional peptides into fibrin gels with factor XIIIa. Bioconjug. Chem.10:75-81 (1999).

Office Action dated May 1, 2018 in U.S. Appl. No. 15/829,440, (105 pages).

The extended European search report dated Feb. 19, 2018 in European Patent Application No. 15821310.8-1109, (11pages).

Communication pursuant to Rules 70(2) and 70a(2) EPC dated Mar. 8, 2018 European Patent Application No. 15821310.8-1109, (1page).

Lam, Jonathan et al., Design of cell-matrix interactions in hyaluronic acid hydrogel scaffolds, Acta Biomaterialia, vol. 10, No. 4, Apr. 1, 2014, pp. 1571-1580, XP55449152.

Lin, Chien-Chi et al., Peg Hydrogels for the Controlled Release of Biomolecules in Regenerative Medicine, Pharmaceutical Research, Kluwer Academic Publishers-Plenum Publishers, NL, vol. 26, No. 3, Dec. 18, 2008, pp. 631-643, XP019686137.

Yongdoo, Part et al., Bovine primary chondrocyte culture in synthetic matrix metalloproteinase-sensitive poly(ethylene glycol)-based hydrogels as a scaffold for cartilage repair, Tissue Engineering, Larchmont, NY, US, vol. 10, No. 3-4, Mar. 1, 2004, pp. 515-522, XP002464246.

Cha, Chaenyung et al., Microfluidics-Assisted Fabrication of Gelatin-Silica Core-Shell Microgels for Injectable Tissue Constructs, dx.doi.org/10.1021/bm401533y, Biomacromolecules 2014, 15, 283-290 (Dec. 2013).

Du et al. Fabrication of Hexagonal-Prismatic Granular Hydrogel Sheets. Langmuir 34(11):3459-3466 (Feb. 2018).

Grainger. Wound healing: Enzymatically crosslinked scaffolds. Nat Mater 14:662-663 (Jul. 2015).

Muehleder et al. Connections matter: channeled hydrogels to improve vascularization. Front Bioeng Biotechnol 2:52 (Nov. 2014).

Nih et al. Injection of Microporous Annealing Particle (MAP) Hydrogels in the Stroke Cavity Reduces Gliosis and Inflammation and Promotes NPC Migration to the Lesion. Adv Mater 29(32):1606471 (Aug. 2017).

Cam et al., Systemic evaluation of natural scaffolds in cutaneous wound healing, J. of Materials Chemistry B, vol. 3:7986-7992 (epub Aug. 21, 2015) (Year: 2015).

Shin, Dissertation Development of Cell-Laden Hydrogels with High Mechanical Strength for Tissue Engineering Applications, MIT, Department of Materials Science and Engineering, 86 pages (Jan. 1, 2014) (Year: 2014).

Smith, Dissertion Engineering Poly(ethylene glycol) Materials to Promote Cardiogenesis, Washington University, St. Louis, Missouri, 142 pages (Aug. 2013) (Year: 2013).

Shih, Thesis, Step-Growth Thiol-ene Photopolymerization to Form Degradable, Cythocompatible and Multi-structural Hydrogels, Purdue University, Indianapolis, Indiana, 92 pages (May 2013) (Year: 2013).

Selimovic et al., Microscale Strategies for Generating cell-encapsulating hydrogels, Polymers, vol. 4:1554-1579 (2012) (Year: 2012).

Hillel et al., Photoactivated Composite Biomaterial for Soft Tissue Restoration in Rodents and in Humans, Sci Transl Med., vol. 3(93):93ra67, 24 pages including Supp., (Jul. 27, 2011) (Year: 2011).

Burdick et al., Hyaluronic Acid Hydrogels for Biomedical Applications, Adv. Mater., vol. 23H41-H56 (2011) (Year: (2011).

Office Action dated Nov. 7, 2018 in U.S. Appl. No. 15/829,440, inventor: Donald R. Griffin, (101 pages).

Examination report No. 1 for standard patent application dated Nov. 30, 2018 in Australian Patent Application No. 2015289474, (6pages).

First Office Action, Japanese Patent Application No. 2017-502712 (corresponding Japanese patent application) dated Jul. 2, 2019 (with English Summary).

Huang et al., Controlled drug release from hydrogel nanoparticle networks, Journal of Controlled Release, 94, 303-11 (2004).

Gaulding et al., Reversible Inter- and Intra-Microgel Cross-Linking Using Disulfides, Macromolecules, 45, 39-45 (2012).

Syrett et al., Functional, star polymeric molecular carriers, built from biodegradable microgel/nanogel cores, Chem. Commun, 47, 1449-1451 (2011).

Aleman et al., IUPAC Recommendations, Pure Appl. Chem., vol. 79(10): 1801-1829 (2007) (Year: 2007).

Chin, UCLA researchers develop new material to accelerate healing, UCLA Newsroom, 3 pages (Jun. 1, 2015), also available at http://newsroom.ucla.edu/releases/ucla-researchers-develop-new-material-to-accelerate-healing (last visited 715120 19) (Year: 2015).

Gan et al., In Situ Gelation of P(NIPAM-HEMA) Microgel Dispersion and Its Applications as Injectable 3D Cell Scaffold, Biomacromolecules vol. 10:1410-1415 (2009) (Year: 2009).

Goyanes et al., Morphometric categorization of the human oocyte and early conceptus, Human Reproduction, vol. 5(5):613-618 (Jul. 1990) (Year: 1990).

Griffin et al., Accelerated wound healing by injectable microporous gel scaffolds assembled from annealed building blocks, Nature Materials, vol. 14:737-744 and 21 pages of Supplemental Information (Published online Jun. 1, 2015) (Year: 2015).

Lodish et al., Molecular Cell Biology, 4th edition. New York: W. H. Freeman; 2000. Section 21.1, Overview of Neuron Neuron Structure and Function, available at www.ncbi.nlm.nih.gov/books/NBK21535/ (last visited Jun. 20, 2019). (Year: 2000).

(56) References Cited

OTHER PUBLICATIONS

Loh et al., Three-Dimensional Scaffolds for Tissue Engineering Applications: Role of Porosity and Pore Size, Tissue Engineering: Part B, vol. 19(6): 485-502 (online Jun. 25, 2013) (Year: 2013).
Malafaya et al., Biomaterials, vol. 29:3914-3926 (Jul. 22, 2008) (Year: 2008).
Maree et al., Morphometric dimensions of the human sperm head depend on the staining method used, Human Reproduction, vol. 25(6):1369-1382 (epub Apr. 17, 2010) (Year: 2010).
Nguyen et al., Clickable Poly(ethylene glycoi)-Microsphere-Based Cell Scaffolds, Macromol Chem Phys., vol. 214(8):948-956 (online Mar. 4, 2013) (Year: 2013).
Parlato et al., Adaptable Poly(ethylene glycol) Microspheres Capable of Mixed-mode Degradation, Acta Biomater., vol. 9(12):9270-9280 (online Aug. 17, 2013) (Year: 2013).
Patel, Poly(ethylene glycol) Hydrogel System Supports Preadipocyte Viability, Adhesion, and Proliferation, Tissue Engineering, vol. 11, No. 9/10, 2005 (8pages).
Sanson et al., Polym. Chem., vol. 1:965-977 (2010) (Year: 2010).
IUPAC Gold Book, "Peptides", 2 pages (Feb. 24, 2014), also available at https://goldbook.iupac.org/html/P/P04479.html (last visited Jul. 1, 2019) (Year: 2014).
Office Action dated Jul. 8, 2019 in U.S. Appl. No. 16/264,466, (91 pages).
Response to an Examiner's Report dated Jun. 21, 2019 in Australian Application No. 2015289474, (21 pages).
Examination report No. 2 for standard patent application dated Jul. 15, 2019 in Australian Application No. 2015289474, (4 pages).
Response to an Examiner's Report dated Oct. 28, 2019 in Australian Application No. 2015289474, (30 pages).
Examination report No. 3 for standard patent application dated Oct. 30, 2019 in Australian Application No. 2015289474, (2 pages).
First Office Action dated Jul. 3, 2019 in Brazilian Patent Application No. BR112017000813-0, (7 pages).
Notification of First Office Action dated Jun. 13, 2019 in Chinese Patent Application No. 2015800494786, (18 pages).
Response to First Office Action dated Sep. 26, 2019 in Chinese Patent Application No. 2015800494786, (8 pages).
Response extended European Search Report dated Sep. 18, 2019 in European Patent Application No. EP15821310.8, (28 pages).
Notice of Rejection dated Mar. 22, 2019 in Japanese Patent Application No. 2017-502712, (17 pages).
Guan, Ying et al., PNIPAM microgels for biomedical applications: from dispersed particles to 3D assemblies, Soft Matter, 2011, vol. 7, pp. 6375-6384.
Huang, Gang et al., Controlled drug release from hydrogel nanoparticle networks, Journal of Controlled release, 2004, vol. 94, pp. 303-311.
Final Office Action dated Jan. 31, 2023 for U.S. Appl. No. 16/077,985, (19 pages).
Examiner's Report dated in Jun. 9, 2022 in Canadian Patent Application No. 2955357, Applicant: The Regents of the University of California, (5 pages).
Response to Examiner's Report dated in Oct. 11, 2022 in Canadian Patent Application No. 2955357, Applicant: The Regents of the University of California, (31 pages).
Final Office Action dated May 19, 2023 for U.S. Appl. No. 16/071,252 (28 pages).
Guan et al., PNIPAM microgels for biomedical applications: from dispersed particles to 3D assemblies. Soft Matter, 2011, 7, 6375-6384, (2011).
Hoare et al., Hydrogels in drug delivery: Progress and challenges, Polymer, 49, 1993-2007, (2008).
Nichols et al., Factors affecting size and swelling of poly(ethylene glycol) microspheres formed in aqueous sodium sulfate solutions without surfactants, Biomaterials, 30 (29):5283-5291, (Oct. 2009).
Park et al., Bovine Primary Chondrocyte Culture in Synthetic Matrix Metalloproteinase-Sensitive Poly(ethylene glycol)-Based Hydrogels as a Scaffold for Cartilage Repair, Tissue Engineering, vol. 10, No. 3/4, (2004).

* cited by examiner

MICROPOROUS ANNEALED PARTICLE GEL SYSTEM

RELATED APPLICATIONS

This Application is a divisional of U.S. application Ser. No. 16/077,985 filed on Aug. 14, 2018, which is a U.S. National Stage filing under 35 U.S.C. § 371 of International Application No. PCT/US2017/017837, filed Feb. 14, 2017, which claims priority to U.S. Provisional Patent Application No. 62/295,933 filed on Feb. 16, 2016, which are hereby incorporated by reference. Priority is claimed pursuant to 35 U.S.C. § § § 119, 120, 371 and any other applicable statute.

STATEMENT REGARDING FEDERALLY SPONSORED RESEARCH AND DEVELOPMENT

This invention was made with government support under Grant Number NS094599, awarded by the National Institutes of Health. The government has certain rights in the invention.

TECHNICAL FIELD

The technical field generally relates to therapeutic hydrogels and in particular microporous hydrogels that are delivered to a human or mammalian subject.

BACKGROUND

Vaccination against target antigens is a crucial part of human health worldwide, and provides the main avenue by which disease is combatted and controlled within the human population. Vaccine technology relies on two critical molecular components: (i) the adjuvant—or immune stimulatory component and (ii) the antigen—the desired target for immunity via antibody production (i.e., acquired immunity). Current state-of-the-art in vaccine administration utilizes an intramuscular injection of a mixture of these two critical components to stimulate antibody production against the target antigen. This technique requires the use of booster shots (repeat doses) to generate a sustained antibody production against the target antigen. Unfortunately, booster shots require that the vaccine recipient visit their healthcare provider one or more follow-up visits to receive the booster shots. The patient may never return to receive his or her booster shot for any number of reasons (e.g., lack of funds, was never notified that it was needed, etc.). In such a case, the patient may have an ineffective or incomplete immune response to the target antigen. This may put the patient at risk as well as others in the case of communicable diseases.

Vaccine technological development has focused in improvement of the two main components: antigen and adjuvant. The advent of genetic engineering and its acceleration in biotechnology during the 1970s and 1980s provided ways of tailoring the antigen to improve its effectiveness. Within the past 15 years, the viral life cycle has been used as an antigen presenting mechanism in humans, where viruses engineered to be safe for human injection (or viral like particles, VLPs, incapable of replication) harbor the antigens of interest and, through their normal life cycle, lead to antigen presentation to the host immune system and antibody production or T cell maturation. Adjuvant engineering has seen some improvement, beginning with mineral salts of calcium phosphate or aluminum, and more recently the squalene-containing oil-in-water emulsion adjuvant MF59® stabilized by Tween 80 and Span 85, from Novartis and an alternative emulsion (AS03), available from Glaxo Smith-Kline. These techniques have shown to increase immunogenicity, but only in certain clades (distinct virus groupings). Newer experimental techniques for suppressing a host immune response to an autoantigen (a host "self" antigen that is aberrantly targeted in an autoimmune disorder) are also being developed. Although all of these vaccination techniques focus on improving what are the critical components of the injected vaccine, they do not address the inherent difficulty of controlling what happens to the adjuvants and antigens after they are injected into the host. The capability to address and control this stage of the immunization process will be critical to develop high efficiency vaccines that do not require boosters or vaccines directed to the host's own cell subpopulations (such as cancerous cells within the body).

SUMMARY

In one embodiment, a system is disclosed that includes a plurality of microgel particles, wherein at least one microgel particle of the plurality of microgel particles comprises a hydrogel backbone and one or more annealing components. The system further includes an annealing agent configured to couple the one or more annealing components of two or more microgel particles of the plurality of microgel particles to form a covalently-stabilized scaffold of microgel particles having pores formed between the microgel particles, wherein the pores are substantially devoid of hydrogel.

In one embodiment, a hydrogel-based material (also referred to herein in some instances as Microporous Annealed Particle or MAP gels) that is formed using annealed microgel particles that form a microporous scaffold structure in situ within the body that enables one to generate synthetic, injectable therapies for immune cell modulation over sustained periods. In one specific embodiment, the invention provides for high affinity antibody production against a target antigen with a single injection, mitigating the need for booster immunization. The antigen may be contained on or within the microgel particles that are used to form the scaffold. An adjuvant may also be contained on or within the microgel particles to assist in the immune response. The use of the hydrogel-based material in conjunction with molecules or moieties that affect the immune response in a subject include all methods of immune modulation including but not limited to: vaccination, immunotherapy platforms for cancer therapy, and immune suppression to aid in organ transplant acceptance without systemic immune suppression.

In one aspect of the invention, the hydrogel-based material includes microgel particles that are engineered to contain or present molecules or moieties that will provoke, stimulate, direct, and/or modulate an immunological response in the subject (e.g., human or other mammal). The microgel particles may also be engineered to contain antigens to provide or initiate the immune response. The microgel particles are delivered intradermally, subdermally, intratumorally, intralesionally, or intramuscularly via injection or implantation. The microgel particles are annealed in situ either through an endogenous annealing agent or an exogenous annealing agent. The delivered microgel particles form a microporous scaffold that provides for the continuous, time-encoded, modulation of the immune system. The microporous scaffold is capable of ingrowth of vascular and/or lymphatic vessels, recruitment of immune cells, stimulation of antibody production, and T-cell maturation that are targeted to the antigen. The microporous scaffold is capable of inducing the formation of all tissue necessary to generate lymph tissue, including lymph nodes in vivo. In this regard, the microporous scaffold may be used, in one embodiment, as a type of artificial lymph node.

In one embodiment, a hydrogel material for modulating an immune response in a human subject or other mammal includes a collection of microgel particles including one or more network crosslinker components, wherein the microgel particles are spherical in shape and have diameters within the range of about 50 µm to 200 µm. The hydrogel material includes an endogenous or exogenous annealing agent that links the microgel particles together at points of physical contact in situ to form a covalently-stabilized scaffold of microgel particles having interstitial spaces formed between the microgel particles and wherein the collection of microgel particles further include at least one of an antigen and an adjuvant. In some embodiments, the microgel particles may include both an antigen and an adjuvant. For example, the antigen and/or adjuvant may be chemically bound to the microgel particles. The adjuvant, when present on or within the microgel particles may be covalently bound to the microgel particles, caged within the hydrogel scaffold, or passively diffused into the microgel particles (e.g., just prior to injection or delivery). In some embodiments, the hydrogel may be biodegradable or non-biodegradable.

In another embodiment, a hydrogel material for modulating an immune response in a human subject or other mammal includes a heterogeneous collection of microgel particles of different types including one or more network crosslinker components, wherein the heterogeneous collection of microgel particles, when exposed to an endogenous or exogenous annealing agent, links the microgel particles together at points of physical contact in situ to form a covalently-stabilized scaffold of the heterogeneous collection of microgel particles having interstitial spaces formed between the microgel particles, wherein a first type of microgel particle is non-degradable or degradable over a timescale in excess of 8 weeks (e.g., about 8 to about 12 weeks) and wherein a second type of microgel particle is biodegradable, and wherein the collection of microgel particles of the second type further includes at least one of an antigen and an adjuvant.

In another embodiment, a method of using any of the hydrogel materials described herein includes injecting the collection of microgel particles into tissue of the human subject or other mammal. The hydrogel may be delivered intradermally, subdermally, intratumorally, intralesionally, or intramuscularly via injection or implantation. In other embodiments, the hydrogel material is injected into a tumor or cancerous tissue. In still other embodiments, the hydrogel material is injected or otherwise applied at a site surrounding transplant tissue or a transplanted organ.

DETAILED DESCRIPTION OF THE ILLUSTRATED EMBODIMENTS

Figure 1A:
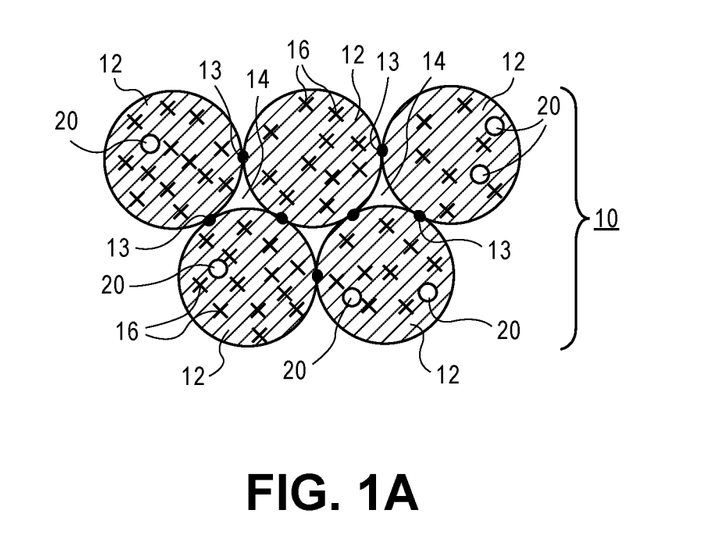
FIG. 1A illustrates an annealed hydrogel material for modulating an immune response in a human subject or other mammal.

FIG. 1A illustrates a portion of the formed three-dimensional scaffold 10 that is formed by a plurality of annealed microgel particles 12. The microgel particles 12 are secured to one another at points of physical contact via annealing connections 13 as illustrated in FIG. 1A using an annealing agent. An endogenous or exogenous (e.g., located in the applicator device) annealing agent then links the microgel particles 12 together in situ to form a covalently-stabilized scaffold of microgel particles 12 having interstitial spaces therein. The annealing agent may include, for example, Factor XIIIa (or Factor XIII with thrombin which generates activated Factor XIII or Factor XIIIa), Eosin Y, a free radical transfer agent, or some combination thereof. The annealing agent may also be present at the delivery site of the microgel particles 12 (i.e., endogenous annealing agent).

FIG. 1A illustrates the microgel particles 12 having a spherical shape. However, it should be understood that the microgel particles 12 may have non-spherical shapes as well, as long as the particle shape enables the formation of a packaged aggregate with microscale length (>~5 µm) interstitial spaces 14. The interstitial spaces therein 14 are voids that form micropores within the larger scaffold 10. The voids may contain an aqueous solution but do not contain any polymer material. The network of interstitial spaces or voids 14 located between annealed microgel particles 12 have dimensions and geometrical profiles that permit the infiltration, binding, and growth of cells and tissue. In particular, in some embodiments, immune cells from the subject's body are able to freely infiltrate through the scaffold 10 using the interstitial spaces 14.

Figure 1B:
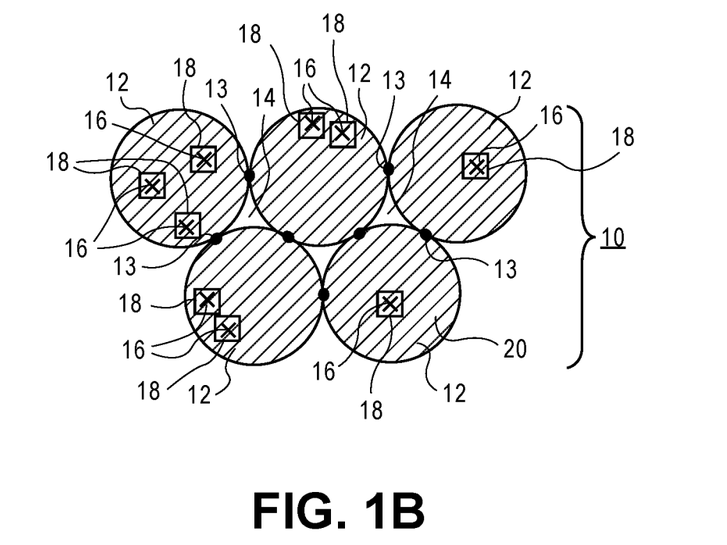
FIG. 1B illustrates an annealed hydrogel material for modulating an immune response in a human subject or other mammal that includes nanoparticles contained within the microgel particles. The nanoparticles contain an antigen or an adjuvant.

FIG. 1A further illustrates an antigen 16 that, in one embodiment, is conjugated to at least some of the microgel particles 12 that form the scaffold 10. The antigen 16 may include a molecule (or multiple molecules), molecular fragment, or moiety that provokes or triggers an immune response. In one embodiment, the antigen 16 is chemically bound to the microgel particles 12. In other instances, the antigen 16 may be mechanically but not chemically bonded to the microgel particles 12. In another embodiment, the antigen 16 may be loaded within degradable nanoparticles 18 that are contained within the microgel particles 12 during fabrication as illustrated in FIG. 1B. Depending on the structure and composition of the hydrogel scaffold 10, all of the microgel particles 12 may have antigen 16 contained therein or thereon. In other embodiments, however, only some of the microgel particles 12 may have antigen 16 contained therein or thereon.

According to invention, at least some of the microgel particles 12 contain, either in addition or alternative to the antigen 16, an adjuvant 20. An adjuvant 20, as used herein, is a molecule, molecular fragment, or moiety that modifies or modulates (e.g., upregulates or downregulates) an immune response. The adjuvant 20, in some embodiments, may promote an immune response. In other embodiments, the adjuvant 20 may suppress or inhibit an immune response. In one embodiment, the adjuvant 20 is chemically bound to the microgel particles 12. In other instances, the adjuvant 20 may be mechanically but not chemically bonded to the microgel particles 12. In other instances, the adjuvant 20 may be infused or dispersed within the hydrogel material that forms the microgel particles 12. In another embodiment, the adjuvant 20 may be loaded within degradable nanoparticles 18 that are contained within the microgel particles 12 during fabrication as illustrated in FIG. 1B (with adjuvant 20 replacing the antigen 16). In some embodiments of the hydrogel scaffold 10, all of the microgel particles 12 may have adjuvant 20 contained therein or thereon. In other embodiments, however, only some of the microgel particles 12 may have adjuvant 20 contained therein or thereon.

In one aspect of the subject matter described herein, the microporous gel system uses microgel particles 12 having diameter dimensions within the range from about 50 µm to about 200 µm with the microgel particles 12 being monodisperse in size with coefficient of variations less than 25% in size. The microgel particles 12 may be made from a hydrophilic polymer, amphiphilic polymer, synthetic or natural polymer (e.g., poly(ethylene glycol) (PEG), poly(propylene glycol), poly(hydroxyethylmethacrylate), hyaluronic acid (HA), gelatin, fibrin, chitosan, heparin, heparan, and synthetic versions of HA, gelatin, fibrin, chitosan, heparin, or heparan). In one embodiment, the microgel particles 12 are made from any natural (e.g., modified HA) or synthetic polymer (e.g., PEG) capable of forming a hydrogel. In one or more embodiments, a polymeric network and/or any other support network capable of forming a solid hydrogel construct may be used. Suitable support materials for most tissue engineering/regenerative medicine applications are generally biocompatible and preferably biodegradable. Examples of suitable biocompatible and biodegradable supports include: natural polymeric carbohydrates and their synthetically modified, crosslinked, or substituted derivatives, such as gelatin, agar, agarose, crosslinked alginic acid, chitin, substituted and cross-linked guar gums, cellulose esters, especially with nitrous acids and carboxylic acids, mixed cellulose esters, and cellulose ethers; natural polymers containing nitrogen, such as proteins and derivatives, including cross-linked or modified gelatins, and keratins; vinyl polymers such as poly(ethyleneglycol)acrylate/methacrylate/vinyl sulfone/maleimide/norbornene/allyl, polyacrylamides, polymethacrylates, copolymers and terpolymers of the above polycondensates, such as polyesters, polyamides, and other polymers, such as polyurethanes; and mixtures or copolymers of the above classes, such as graft copolymers obtained by initializing polymerization of synthetic polymers on a preexisting natural polymer. A variety of biocompatible and biodegradable polymers are available for use in therapeutic applications; examples include: polycaprolactone, polyglycolide, polylactide, poly(lactic-co-glycolic acid) (PLGA), and poly-3-hydroxybutyrate. Methods for making networks from such materials are well-known.

In one or more embodiments, the microgel particles 12 further include covalently attached chemicals or molecules that act as signaling modifications that are formed during microgel particle 12 formation. Signaling modifications includes the addition of, for example, adhesive peptides, extracellular matrix (ECM) proteins, and the like. Functional groups and/or linkers can also be added to the microgel particles 12 following their formation through either covalent methods or non-covalent interactions (e.g., electrostatic charge-charge interactions or diffusion limited sequestration). Crosslinkers are selected depending on the desired degradation characteristic. For example, crosslinkers for microgel particles 12 may be degraded hydrolytically, enzymatically, photolytically, or the like. In one particular preferred embodiment, the crosslinker is a matrix metalloprotease (MMP)-degradable crosslinker.

Examples of these crosslinkers are synthetically manufactured or naturally isolated peptides with sequences corresponding to MMP-1 target substrate, MMP-2 target substrate, MMP-9 target substrate, random sequences, Omi target sequences, Heat-Shock Protein target sequences, and any of these listed sequences with all or some amino acids being D chirality or L chirality. In another embodiment, the crosslinker sequences are hydrolytically degradable natural and synthetic polymers consisting of the same backbones listed above (e.g., heparin, alginate, poly(ethyleneglycol), polyacrylamides, polymethacrylates, copolymers and terpolymers of the listed polycondensates, such as polyesters, polyamides, and other polymers, such as polyurethanes).

In another embodiment, the crosslinkers are synthetically manufactured or naturally isolated DNA oligos with sequences corresponding to: restriction enzyme recognition sequences, CpG motifs, Zinc finger motifs, CRISPR or Cas-9 sequences, Talon recognition sequences, and transcription factor-binding domains. Any of the crosslinkers from the listed embodiments above are activated on each end by a reactive group, defined as a chemical group allowing the crosslinker to participate in the crosslinking reaction to form a polymer network or gel, where these functionalities can include: cysteine amino acids, synthetic and naturally occurring thiol-containing molecules, carbene-containing groups, activated esters, acrylates, norbornenes, primary amines, hydrazides, phosphenes, azides, epoxy-containing groups, SANPAH containing groups, and diazirine containing groups. In an alternative embodiment, the microgel crosslinker is non-biodegradable. For example, PEG dithiol, to allow for a long-lasting scaffold with low rates of degradation. Alternatively, the scaffold can be made to be degradable over time by incorporating MMP-degradable crosslinkers to allow resorbability of the material over time, or combinations of degradable and non-degradable microgels can be incorporated at varying stoichiometries (e.g., 1:1, 1:10, 1:20, 1:5) to maintain sufficient material for prolonged immunomodulation while allowing tissue to also regenerate surrounding the material. In still another embodiment, the microgel crosslinker may be specifically designed to photolytically degrade in response to an applied light (e.g., ultra violet light). In this regard, the microgel scaffold 10 that is formed may have a long life that may stay at the site of application for a long period of time (e.g., weeks or months). As noted herein, it has been found experimentally that microgel scaffolds 10 that are not biodegradable tend to have better tissue ingrowth properties. Should the need arise to remove the microgel scaffold 10, the subject area may be illuminated with light for a period of time to accelerate and/or promote the breakdown of the microgel scaffold 10. Examples of crosslinkers that may be degraded with the application of light include macromers incorporating o-nitrobenzyl groups such as those disclosed in Griffin et al., Photodegradable macromers and hydrogels for live cell encapsulation and release, J. Am Chem Soc., 134(31), pp. 13103-7 (2012) as well as light degradable functionalities disclosed in Yanagawa et al., Partially photodegradable hybrid hydrogels with elasticity tunable by light irradiation, Colloids Surf B Biointerfaces, 126, pp. 575-9 (2015); and Shin et al., Photodegradable hydrogels for capture, detection, and release of live cells, Angew Chem Int Ed. Engl., 53(31), pp. 8221-4 (2014), all of which are incorporated herein by reference.

In one embodiment, the chemistry used to generate microgel particles 12 allows for subsequent annealing and scaffold formation through radically-initiated polymerization. This includes chemical-initiators such as ammonium persulfate combined with Tetramethylethylenediamine. Alternatively, photoinitators such as Irgacure® 2959 or Eosin Y together with a free radical transfer agent such as a free thiol group (used at a concentration within the range of 10 μM to 1 mM) may be used in combination with a light source that is used to initiate the reaction as described herein. One example of a free thiol group may include, for example, the amino acid cysteine, as described herein. Of course, peptides including a free cysteine or small molecules including a free thiol may also be used. Another example of a free radical transfer agent includes N-Vinylpyrrolidone (NVP).

Alternatively, Michael and pseudo-Michael addition reactions, including α,β-unsaturated carbonyl groups (e.g., acrylates, vinyl sulfones, maleimides, and the like) to a nucleophilic group (e.g., thiol, amine, aminoxy) may be used to anneal microgel particles 12 to form the scaffold. In another alternative embodiment, microgel particle formation chemistry allows for network formation through initiated sol-gel transitions including fibrinogen to fibrin (via addition of the catalytic enzyme thrombin).

Functionalities that allow for particle-particle annealing are included either during or after the formation of the microgel particles 12. In one or more embodiments, these functionalities include α,β-unsaturated carbonyl groups that can be activated for annealing through either radical initiated reaction with α,β-unsaturated carbonyl groups on adjacent particles or Michael and pseudo-Michael addition reactions with nucleophilic functionalities that are either presented exogenously as a multifunctional linker between particles or as functional groups present on adjacent particles. This method can use multiple microgel particle 12 population types that when mixed form a scaffold 10. For example, microgel particle of type X presenting, for example, nucleophilic surface groups can be used with microgel particle type Y presenting, for example, α,β-unsaturated carbonyl groups. In another embodiment, functionalities that participate in Click chemistry can be included allowing for attachment either directly to adjacent microgel particles 12 that present complimentary Click functionalities or via an exogenously presented multifunctional molecule that participates or initiates (e.g., copper) Click reactions.

The annealing functionality can include any previously discussed functionality used for microgel crosslinking that is either orthogonal or similar (if potential reactive groups remain) in terms of its initiation conditions (e.g., temperature, light, pH) compared to the initial crosslinking reaction. For example, if the initial crosslinking reaction consists of a Michael-addition reaction that is temperature dependent, the subsequent annealing functionality can be initiated through temperature or photoinitiation (e.g., Eosin Y, Irgacure®). As another example, the initial microgels may be photopolymerized at one wavelength of light (e.g., ultraviolet with Irgacure®), and annealing of the microgel particles 12 occurs at the same or another wavelength of light (e.g., visible with Eosin Y) or vice versa. Besides annealing with covalent coupling reactions, annealing moieties can include non-covalent hydrophobic, guest/host interactions (e.g., cyclodextrin), hybridization between complementary nucleic acid sequences or nucleic acid mimics (e.g., protein nucleic acid) on adjoining microgel particles 12 or ionic interactions. An example of an ionic interaction would consist of alginate functionality on the microgel particle surfaces that are annealed with Ca2+. So-called "A+B" reactions can be used to anneal microgel particles 12 as well. In this embodiment, two separate microgel types (type A and type B) are mixed in various ratios (between 0.01:1 and 1:100 A:B) and the surface functionalities of type A react with type B (and vice versa) to initiate annealing. These reaction types may fall under any of the mechanisms listed herein.

In one particular hydrogel scaffold 10 composition, the microgel particles 12 can be formed using 4-arm poly (ethylene glycol) vinyl sulfone (PEG-VS) backbone (20 kDa) that has been pre-modified with oligopeptides for cell adhesive properties (e.g., RGD) and surface/tissue annealing functionalities (e.g., K and Q peptides) along with a crosslinker, which may include a di-cysteine modified Matrix Metallo-protease (MMP) substrate. Microgel particles 12 can be formed using a multi-inlet droplet generation device such as that disclosed in U.S. Patent Application Publication No. 2016/0279283, which is incorporated by reference herein. Generally, a first inlet is used to deliver the PEG-VS backbone that is functionalized while a second inlet is used to deliver the crosslinker while a third inlet delivers unmodified PEG-VS to prevent upstream mixing of the reagents relative to the droplet generation region. The microgel particles 12 may be functionalized with antigen 16 or adjuvant 20. Alternatively, prior to formation of the microgel particles, the PEG-VS may be functionalized with the antigen 16 or adjuvant 20 prior to the formation of the microgel particles 12. In this embodiment, just prior to delivery, the slurry may be mixed with FXIII and thrombin. The thrombin activates FXIII to FXIIIa which is responsible for annealing and linking of the K and Q peptides on adjacent microgel particles 12.

The hydrogel scaffold 10 described herein can be used both as a tissue growth scaffold and an immune modulatory system. The technology accomplishes these goals in two components:

Porosity

The void sizes and geometry (although not spherical pores; the length scales of the void regions between packed microgel particles 12 spans ~2-20 μm) of the linked assembly of microgel particles 12 or scaffold 10 enables vascular and lymphatic ingrowth and prevents a foreign body response (e.g., the scaffold 10 is not surrounded and encapsulated by foreign body giant cells). Each of the microgel particles 12 is in the size range between 50-200 micrometers in diameter, and preferably monodisperse with coefficient of variations less than 25% in size. The controlled porosity in the injectable material enables large, mature vessel formation both of vascular and lymphatic nature. The presence of both of these tissue types is critical for rapidly addressing and modulating immune cells circulating in the vascular and lymphatic systems. The ability of immune cells to freely infiltrate through the microporous network of the material forming the scaffold 10 also prevents fibrous encapsulation of the injected scaffold 10 which would be counterproductive in further developing adaptive immune recognition. In addition, the creation of a scaffold 10 of networked microgel particles 12 into a tumor site and vascular ingrowth can also enable immune cell infiltration in a normally immunosuppressive tumor microenvironment that may contain chemical or physical barriers to immune cell infiltration.

Synthetic Material with Embedded Modulation Mechanisms

Figure 1C:
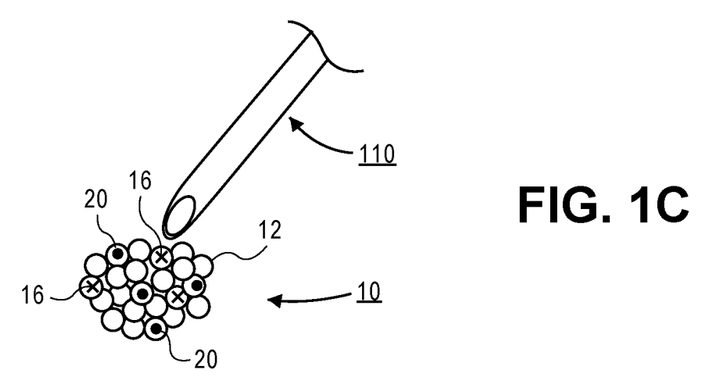
FIG. 1C illustrates the injection and annealing in situ of a hydrogel material for modulating an immune response in a human subject or other mammal.
Figure 1D:
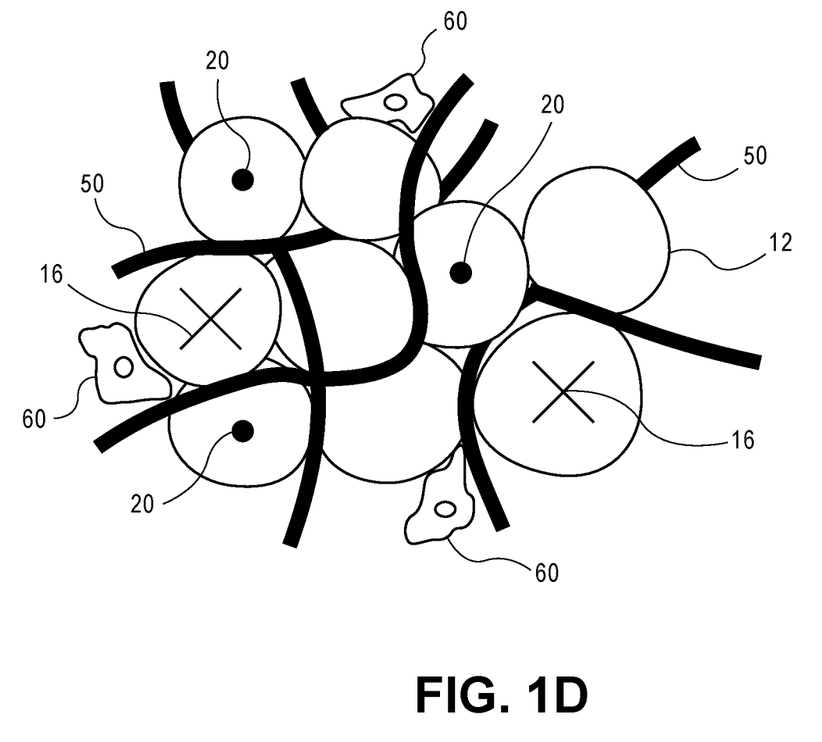
FIG. 1D illustrates vascular and lymphatic vessel ingrowth to boost the recruitment of immune cells.

The microgel particles 12 that are used to create the injectable scaffold 10 are pre-loaded, either within the solvent associated with the hydrogel or covalently linked to the hydrogel backbone, with antigens 16 or adjuvants 20, or both antigens 16 and adjuvants 20. FIG. 1C illustrates a delivery device 110 (e.g., syringe with needle) delivering microgel particles 12 that are used to form a scaffold 10 that includes both antigens 16 and adjuvants 10. The release profiles of the antigens 16 and/or adjuvants 20 is engineered according to the desired release rate. The release profile may be rapid, release slowly over time, or release after an external stimulus is applied (e.g., light such as ultraviolet light). This enables the hydrogel scaffold 10 based system to be tuned to achieve the optimal immune response and training to produce the maximum amount of high affinity antibodies and T cells against the target antigen (for applications where the immune response is enhanced). FIG. 1D illustrates an annealed hydrogel scaffold 10 that includes vascular/lymphatic vessel 50 growth therein as well as the recruitment of immune cells 60.

In one embodiment, the hydrogel-based scaffold 10 described herein can achieve both vascular/lymphatic ingrowth while enabling controlled release of molecules (e.g., antigens 16 or adjuvants 20) through the initial formation of the scaffold 20 from a heterogeneous population of microgel particles 12. In this embodiment, different types of microgel particles 12 are used to form the scaffold 10. For example, in one embodiment a first type of microgel particles 12 are those microgel particles 12 that are completely non-degradable or degradable over a longer timescale (weeks to months), and act as a porous scaffold 12 for ingrowth. This may be, in some embodiments, a majority of the number of microgel particles 12 forming the scaffold 10. The remainder of the microgel particles 12, which are dispersed randomly within the injected population of microgel particles 12 of all types, are designed as degradable release depots of either antigen 16, adjuvant 20, or both. This release can be coupled to the degradation of the microgel particles 12 of the second type via cellular ingrowth and matrix remodeling through matrix metalloproteinase or serine protease peptide substrate linkers, or independent of the rate of cellular degradation based on hydrolysable bonds (e.g., ester or anhydride). In this embodiment, the system starts out as an injectable slurry of multiple types of hydrogel microgel particles 12 which are cross-linked to each other in situ and enables delivery similar to current vaccines.

Embedding Adjuvant and Antigen Within MAP Gels

By integrating both the antigen 16 and the adjuvant 20 into the microgel particles 12 either during fabrication or after fabrication but prior to injection/implantation, the lifetime or lifespan of the antigens 16 and the adjuvants 20 can be controlled, and the immune response tailored. Specifically, adjuvants 20 such as CpG (Cytosine-poly-guanine) DNA strands can be either covalently tethered to the microgel particles 12, caged within the microgel particles 12 by introduction during initial microgel particle crosslinking, or passively diffused into the microgel particles 12 following crosslinking but prior to injection or delivery. Incubation of microgel particles 12 in solution and the adjuvants 20 would enable diffusion into the nanoporous regions within the hydrogel for example. Caging or affinity of CpG DNA within the microgel particles 12 can also be enabled by including counter-ion polymeric regions in the microgel particles 12, for example by covalently linking poly-lysine moieties. Combinations of one or more adjuvants 20 can also be used: TLR2 agonist (Pam3Cys-Ser-Lys4), double stranded RNA (TLR3 agonist), monophosphoryl Lipid-A (TLR4 agonist), flagellin (TLR5 agonist), thiazoquinoline or imidazoquinoline (TLR7, TLR8, or TLR7/8 agonist compounds), CpG-containing DNA (TLR9 agonist) and non-CpG DNA, cyclic guanine monophosphate adenosine (cGAMP), dicyclic adenosine monophosphate, dicyclic guanidine monophosphate (all cGAS/STING agonists), or cytokine agents (activating: Interleukin-2, IL-12, IL-15, IL-32, interferon-alpha, beta, or gamma, or TNF-alpha; or inhibitory cytokines Transforming growth factor-beta, IL-10, or IL-37) whether as a mixture or alone. Traditional adjuvants 20 such as mineral salts of calcium phosphate or aluminum can also be used.

Additionally, co-stimulatory (CD28, ICOS-ligand, 4I-BB, CD40L, etc.) or coinhibitory (cytotoxic T lymphocyte antigen-4, programmed death-1 ligands, CD271 or CD274, TIGIT, etc.) molecules can be coated on the microgel particles 12 to stimulate or inhibit immunity to the peptides. Another type of molecule that could be added includes checkpoint inhibitor antibodies (anti-CTLA-4, anti-PD-1 anti-TIGIT, etc.) to locally prevent the induction of immune checkpoint responses, which may limit the generation of immune responses to the vaccine. Additionally, chemokines that drive lymphoneogenesis, such as CXCL-13, CCL-22, CXCL-12, CCL-21, and lymphotoxin-beta can be embedded into the microgel particles 12 to develop new lymph node structures (lymphoneogenesis) as tissue grows into the microporous scaffold 10. Any combination of antigens 16 with immunostimulatory adjuvants 20 or immunoinhibitory adjuvants 20 can be combined to create the immunostimulatory or immunoinhibitory vaccine. The antigen(s) 16 are also linked to the microgel particles 12 prior to injection/implantation. Living cells that have anti-inflammatory potential, such as mesenchymal stem cells, multipotent adult progenitor cells, or autologous regulatory T cells, can also be delivered with the slurry or mixture of microgel particles 12, wherein these cells are not encapsulated within the actual microgel particles 12 themselves, but exist between microgel particles 12 in the interstitial spaces 14. When the microgel particles 12 are annealed, the cells are incorporated into the interstitial spaces 14 of the microporous scaffold 10 and can adhere and migrate within this network to perform functions (e.g., tissue or vessel regrowth, immune response, etc.). This is not the case when cells are embedded within the microgel particles 12. These cells may suppress an immune response as part of an immunoinhibitory vaccine, or to provide structure for a developing lymph node-like tissue (lymphoneogenesis).

In one embodiment, the antigen 16 and/or adjuvant 20 may include a protein or peptide that can be bound or covalently linked to the surface of the microgel particles 12 following the formation of the individual microgel particles 12 but prior to annealing to form the porous hydrogel scaffold 10. This is an ideal delivery modality for drugs that do not require internalization for action such as a Toll-like receptor 2 (TLR2) agonists, checkpoint inhibitor antibodies, or molecules that work on the cell surface such as co-stimulatory molecules. The antigen 16 and/or adjuvant 20 can also be loaded within degradable nanoparticles 18 that are contained within the microgel particles 12 during fabrication as seen in FIG. 1B. For example, poly(lactic acid) copolymer with poly(glycolic acid) (PLGA) can be dispersed in an emulsion to form nanoparticles with embedded agents and drugs. See Bala et al., PLGA nanoparticles in drug delivery: the state of the art, Crit Rev Ther Drug Carrier Syst, 21(5), pp. 387-422 (2004), which is incorporated herein by reference. For example, the polymer is first dissolved in dicholoromethane, agent or drug is added to this solution. This polymer-drug solution is then dispersed in a larger volume of water and polyvinyl alcohol and stirred vigorously to create a nano-emulsion. The nano-emulsion is then subjected to solvent removal by evaporation or extraction to create solidified PLGA nanoparticles 18. Alternative solvent pairs can be used to create the emulsion for water soluble agents and drugs (e.g., acetonitrile/n-hexane with Span surfactant). The use of nanoparticles 18 has the advantage that high amounts of antigen 16 and/or adjuvant 20 can be loaded and the release profile can be controlled from days to months.

The antigen 16 and/or adjuvant 20 can also be directly conjugated to the microgel particle 12 backbone through a degradable linker such that release can be locally triggered. For example, the immobilization of drugs to hydrogels through MMP or other protease-degradable linkers results in release only when MMP secreting cells (or cells secreting the protease targeting the specific crosslinker sequence) infiltrate the scaffold 10. Immobilized DNA oligos (ODN) may be released using this approach. Lastly, the desired payload can be encapsulated within the microgel particles 12 during generation. The release profile in this case is directly related to the molecular weight of the payload and the crosslinking density of the microgel particles 12. Because TLR2 is a cell surface receptor, but TLR9 and STING agonists require internalization, two separate linking and delivery approaches are used to achieve the most robust activation. TLR2 agonist (Pam3cys4) can be bound to the surface of the microgel particle 12 to provide activation of immune cells initially infiltrating the hydrogel. CpG- and non-CpG-DNA nanoparticles can be attached to the degradable cross linkers and therefore become freely soluble upon cleavage of the linkage by MMPs.

Once injected or otherwise implanted into the body, the microgel particles 12 anneal via an annealing agent and/or stimulus (light, enzymatic, or chemical) and form a microporous scaffold 10 that may also be linked (mechanically and/or chemically) to the surrounding tissue. The microporous nature of the scaffold 10 enables fully matured vasculature to form within the scaffold very quickly (within 5 days) (see e.g., Griffin et al., Accelerated wound healing by injectable gel scaffolds assembled from annealed building blocks, Nature Materials, 14, 737-744 (2015), which is incorporated by reference herein). This allows circulating immune cells to have direct access to the contents of the scaffold 10, and as these immune cells travel into the scaffold 10, they are activated by the controlled elution or presence on the surface of the microgel particles 12 of the molecules of adjuvant 20. Subsequently, these activated immune cells (e.g., antigen presenting cells) will engulf soluble antigen 16 or small (e.g., <1-5 micrometer in diameter to enable phagocytosis) antigen-containing hydrogel particles or particle pieces present within the scaffold 10 and present this, ultimately for generating a robust adaptive immune response against the antigen 16.

The ability to embed controlled release profiles into the scaffold 10, combined with the inherent ability of the scaffold 10 to support fast mature vascular formation, makes this platform an ideal candidate for the next generation of vaccine platforms. In essence, the scaffold 10 acts as a vascularized artificial lymph node that can be used to more efficiently educate the immune system to an antigen 16 of choice.

In one embodiment, the hydrogel particles 12 include one or more sub-populations of pre-fabricated microgel particles 12 of different types. The different types of microgel particles 12 may relate to their respective degrees of degradability. One type of microgel particle 12 may be degradable while another type of microgel particle 12 is non-degradable or slowly degradable. The degradable microgel particles 12 may release molecules of antigen 16 and/or adjuvant 20 both fast and/or slow or a custom-designed rate. In non-degradable or slowly degradable embodiments, the hydrogel particles 12 within the scaffold 10 remain there permanently or for an extended period of time (e.g., more than 12 weeks) to support vascularization.

Figure 2A:
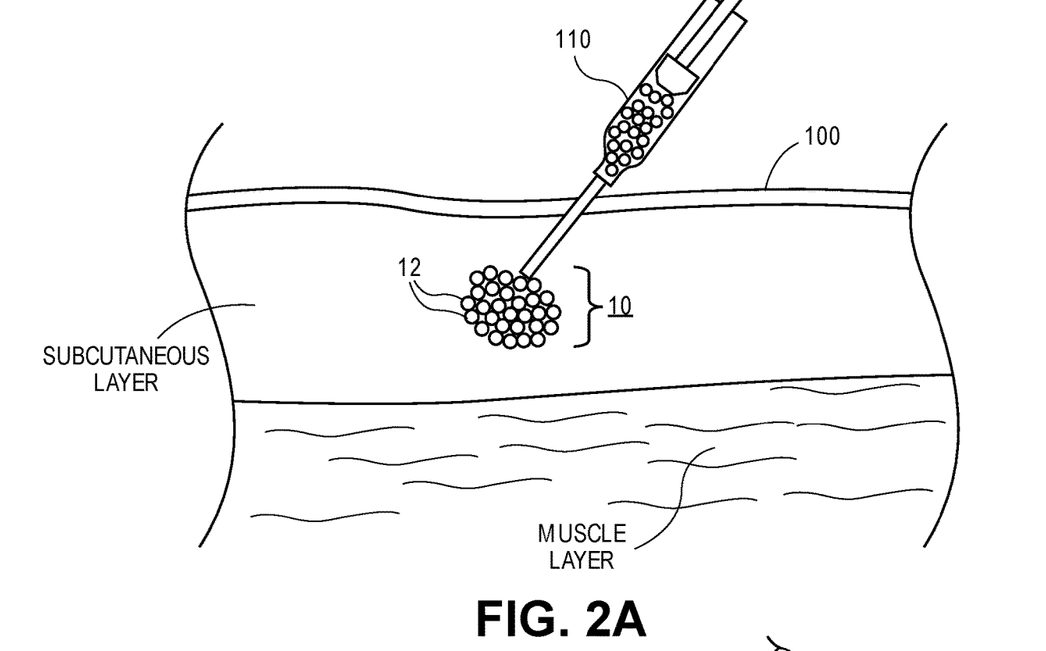
FIG. 2A illustrates the subcutaneous injection of the hydrogel material for modulating an immune response in a human subject or other mammal.

In one embodiment, for example for vaccinations, the hydrogel particles 12 may be delivered subcutaneously under the skin 100 as seen in FIG. 2A. In this embodiment, a delivery device 110 such as syringe is used to deliver the slurry or mixture of hydrogel particles 12 form a scaffold 10 that acts as a synthetic lymph node. Single or multiple antigens 16 and/or adjuvants 20 can be loaded on or into the hydrogel particles 12 as explained herein. This can advantageously simplify the vaccine schedule by providing protection against multiple diseases at once. That is to say a single implanted scaffold 10 may be used to vaccinate an individual for multiple diseases. While FIG. 2A illustrates the subcutaneous delivery of the vaccine scaffold 10, in other embodiments it may also be delivered intradermally, or intramuscularly via injection or implantation.

The hydrogel-based scaffold 10 described herein eliminates the need for booster shots which is helpful for healthcare settings where it is difficult or impossible to return to health care providers to obtain the necessary booster shots. Moreover, this further simplifies vaccine delivery protocols as only a single delivery is needed. By providing antigen 16 that is present for a long period of time (2-3 weeks) in a three-dimensional synthetic lymph node that is formed by the scaffold 10, the platform can accelerate high affinity maturation and antibody diversity.

Figure 2B:
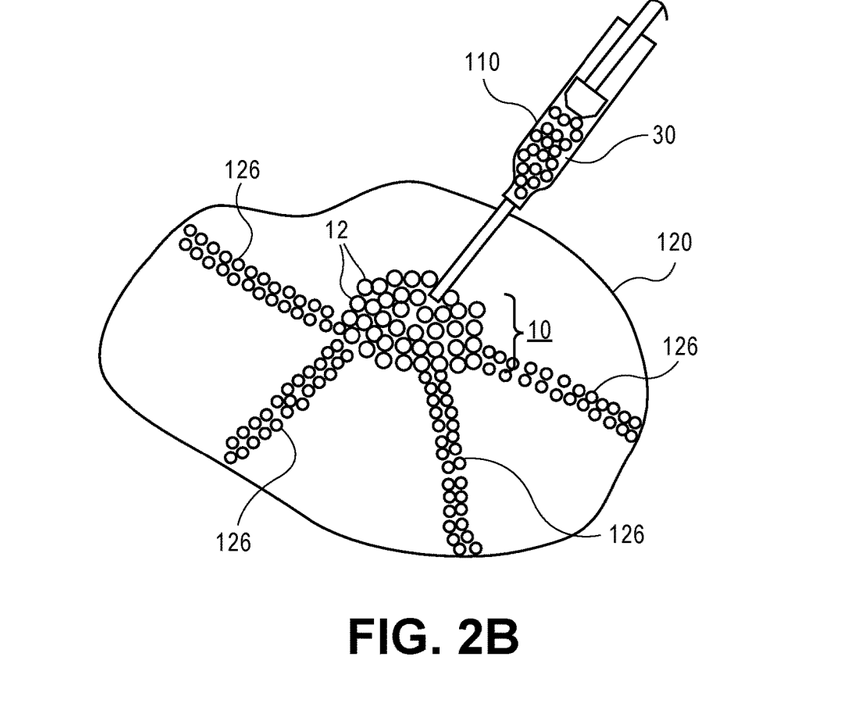
FIG. 2B illustrates the direct injection into a tumor of the hydrogel material for modulating an immune response in a human subject or other mammal.

In another separate embodiment of the invention, the scaffold 10 that is formed using the microgel particles 12 is used for cancer immunotherapy. In this embodiment, the microgel particles 12 are delivered subcutaneously as seen in FIG. 2A or intra-tumorily as seen in FIG. 2B. The intra-tumor delivery approach illustrated in FIG. 2B, the microgel particles 12 are injected inside the solid tumor 120 along with optional chemotherapeutic agents 30. Chemotherapeutic agents can be delivered within the microgel particles 12 or co-injected with the microgel particles 12 (illustrated in FIG. 2B). Alternatively, the microgel particles 12 may be injected into the tumor after the tumor has been subject to radiation. For example, the tumor may be subject to radiation followed by the intra-tumor delivery of microgel particles 12 as few days following the radiation treatment.

The microgel particles 12 may be loaded with innate immune adjuvants such as natural toll-like receptor 2 (TLR) agonists (e.g., lipotechoic acid, Lipoarabinomannan, Lipomannan, peptidoglycan), Macrophage-activating lipopeptide-2 (MALP-2); natural TLR/2/dectin 1 agonist: Zymosan; natural or synthetic TLR2/6 ligand; FSL-1; synthetic TLR2 agonists such as Pam2CSK4; synthetic TLR2/TLR1 agonists such as Pam3CSK4; TLR3 agonists such as double stranded RNA, Polyinosine-polycytidylic acid (low or high molecular weight); TLR3 agonists: double stranded RNA, Polyinosine-polycytidylic acid (low or high molecular weight); TLR4 agonists: lipopolysaccharide, lipid A, monophosphoryl lipid A; TLR5 agonist: Flagellin; TLR7 agonist: imiquimod and other imidazoquinolone compounds, adenine analogs, loxoribine; TLR7/8 agonist: single stranded RNAs, poly U containing single stranded RNAs, poly (dT): (thymidine homopolymer), other imidazoquinolone compounds (R848) and benzoazepine analogs; TLR9 agonist: CpG containing DNA oligodeoxynucleotides (Class A:-ODN1585, ODN2216, ODN2336 Class B-ODN 1668, ODN 1826, ODN 2006, ODN 2007, ODN BW006, ODN D-SL01, or Class C ODNs-ODN 2395, ODN M362, ODN D-SL03); RIG-I/mda-5 agonists: 5'ppp-dsRNA, poly-IC (low or high molecular weight); STING agonists: 3'3'-cGAMP, 2'3'-cGAMP, 2'2'-cGAMP, di-cyclic AMP, di-cyclic GMP, di-cyclic UMP, di-cyclic IMP, DMXAA; cGAS/AIM2 agonist: dsDNA (poly dA:dT or poly dC:dG), other viral or bacterial dsDNA; inflammasome inducers: ATP, Alum, chitosan, hemozoin, nigericin, muramyl dipeptide, curdlan AL, pustulan, zymosan, flagellin, poly(dA:dT); cytokines: (Interleukins) IL-2, IL-15, IL-32, IL-33, IL-12, IL-23, IL-6, IL-21, and IL-18; colony stimulating factors: GM-CSF, G-CSF, M-CSF; tumor necrosis factor alpha or beta, lymphotoxin alpha or beta; soluble receptors or blocking antibodies to the following molecules (Ox-40L, CD40L, GITR, PD-1, PD-L1, PD-L2, 4 1-IBB, CD28, CTLA-4). These innate immune adjuvants may be loaded in the microgel particles 12 themselves or in nanoparticles 18 for controlled release applications. In yet another alternative embodiment, the hydrogel scaffold 10 could be applied on or external to the location of cancerous tissue (e.g., tumor margins). As one particular example, the tumor may first be removed and the microgel particles 12 are then injected into the void or area where the tumor was formerly located.

In addition, dying or lysed tumor cells can be used as cancer antigens 16. These dying or lysed tumor cells could be mixed or co-delivered with the microgel particles 12 (or embedded therein). Also, irradiated tumor cells from biopsy or circulating tumor cells (CTCs) can be embedded within the microgel particles 12 or co-injected with the microgel particles 12. Multiple injections of the slurry or mixture of microgel particles 12 with CTCs collected over time can be used to adapt to the latest neoantigens as tumors evolve and progress. Lysate from tumor or circulating tumor cells can be included in the precursor gel solution used for the microgel particles 12 to incorporate antigens. The microgel particles 12 that form the scaffold 10 can also co-deliver therapeutic antibodies (e.g., checkpoint inhibitors) (anti-CTLA-4; ipilimumab, PD-1; nivolumab or pembrolizumab). Because the ability of melanoma patients to respond to checkpoint inhibitor blockade is directly correlated with the ability for cytotoxic T cells to infiltrate into the tumor margin of the melanoma; persistent immune activation within adjuvant-MAP gel tumors will improve efficacy of the adjuvants 20 both in the absence and in the presence of systemic checkpoint inhibitor blockade. This may potentially be useful when vaccinating against viruses as viral infection can induce these immunosuppressive pathways locally, and suppressing the ability of viruses to utilize these immunosuppressive pathways may lead to greater vaccine responses when combined with traditional adjuvants. Further, injection of the microgel particles 12 from the tumor to its periphery (e.g., making pathways 126 as seen in FIG. 2B into the interior of a tumor 120) can mitigate the immunosuppression by tumor microenvironment, and result in increased recruitment of immune cells (e.g., increased recruitment of dendritic cells, enhanced T cell tumor infiltration). This can be accomplished using the needle track that is formed by the syringe or other delivery device that delivers the microgel particles 12 to the interior of the tumor 120. The void spaces 14 of linked microgel particles 12 along this track 126 and adjacent or within the tumor 120 provide routes for blood vessel and immune cell infiltration that were not previously present.

In another embodiment, the microgel particles 12 may be loaded with medicament payloads that are released upon exposure to radiation. Radiation thus may be used both to destroy the tumor as well as initiate the release of a medicament or pharmaceutical. This may include a chemotherapeutic agent or an innate immune adjuvant.

Figure 2C:
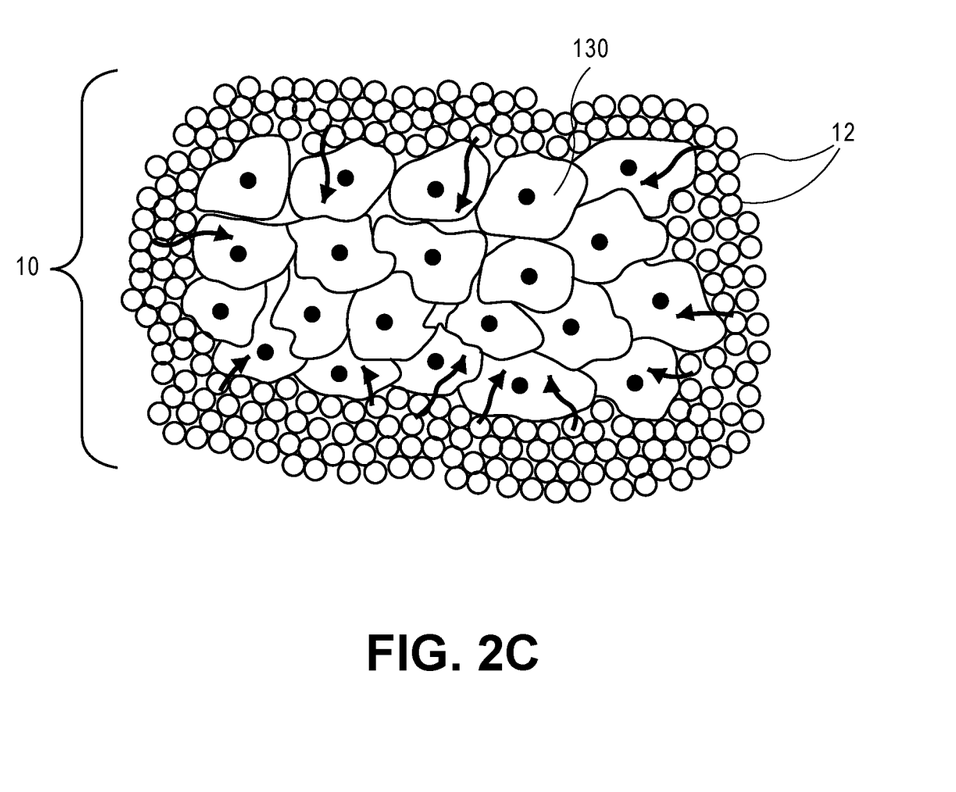
FIG. 2C illustrates hydrogel material for modulating an immune response in a human subject or other mammal that has been injected or otherwise delivered around transplant cells or tissue.

In still another embodiment, with reference to FIG. 2C, the scaffold 10 is used for immune inhibition. In this embodiment, an immunosuppressive agent such as corticosteroids and/or calcineurin inhibitors are locally delivered from the microgel particles 12 (illustrated by arrows) that are flowed in and around a transplanted organ or transplanted tissue 130 (e.g., islet cell transplantation, etc.) to also inhibit immune response to prevent transplantation rejection. This embodiment is illustrated in FIG. 2C. Corticosteroids and calcineurin inhibitors may be loaded inside the microgel particles 12 or chemically bound thereto and are released locally. For example, the microgel particles 12 may release the corticosteroids and/or calcineurin inhibitors in response to biodegradation of the microgel particles 12. Alternatively, protease-degradable linkers may link these molecules to the microgel particles 12 which are released in the presence of MMP or other protease targeting the specific crosslinker sequence. Co-inhibitory molecules such as CTLA-4, PD-1, TIGIT, and others can be linked to the hydrogel beads as explained herein, providing a further immune inhibiting signal from the hydrogel scaffold 10.

To use the microgel particles 12, a physician or other qualified health care provider obtains a pre-made quantity of microgel particles 12 that will be used to form the hydrogel scaffold 10. These may be made on-site, but preferably are pre-manufactured and stored for later use. These microgel particles 12 are in an un-annealed state and are already populated or infused with the antigen 16 and/or adjuvant 20. In one particular embodiment, the microgel particles 12 are then mixed with an annealing agent (e.g., Factor XIII and thrombin) and loaded into a delivery device such as a syringe 110. The mixture is then injected into the site of application (e.g., under the skin, within a tumor, or surrounding implanted tissue or an organ). While a delivery device such as a syringe 110 is disclosed as a preferred embodiment, in other embodiments, the slurry mixture could be applied using another delivery modality such as a paste that can be applied directly to the site of application using an applicator tool (e.g., applicator stick) or even manually delivered to the site. After the mixture has been delivered, the microgel particles 12 will then anneal to form the hydrogel scaffold 10. The hydrogel scaffold 10 is now available to modulate the subject's immune response (e.g., upregulate or downregulate) as described herein. In vaccine applications, there is no need for return visits for "booster" injections as the hydrogel scaffold 10 has been designed to provide long-lasting immune response. For cancer treatments or applications, repeat injections may be warranted, for example, where phenotypic changes in cancer cells may result in the need to target these slight modifications to adapt to the latest neoantigens.

In alternative embodiments, the slurry mixture of microgel particles 12 may be mixed with other components prior to injection or delivery to the patient. For example, chemotherapeutic agents (alone or in combination) may be combined with the slurry mixture of microgel particles 12 prior to administration. In still another embodiment, the slurry mixture of microgel particles 12 may be combined with cells (e.g., live or dead cells) as explained herein. In still, another embodiment, the slurry mixture of microgel particles 12 is mixed with an immunosuppressive agent (or multiple agents).

While embodiments of the present invention have been shown and described, various modifications may be made without departing from the scope of the present invention. The invention, therefore, should not be limited, except to the following claims, and their equivalents.

What is claimed is:

1. A system, comprising:
   (a) a plurality of microgel particles, wherein at least one microgel particle of the plurality of microgel particles comprises a hydrogel backbone and one or more annealing components; and
   (b) an annealing agent configured to couple the one or more annealing components of two or more microgel particles of the plurality of microgel particles to form a covalently-stabilized scaffold of microgel particles having pores formed between the microgel particles, wherein the pores are on the 10 micrometer scale and are substantially devoid of hydrogel.

2. The system of claim 1, wherein at least one pore of the pores formed between the plurality of microgel particles comprises a diameter of about 10 micrometers.

3. The system of claim 1, wherein at least one microgel particle of the plurality of microgel particles comprises a diameter that is at least or about 50 micrometers.

4. The system of claim 1, wherein the hydrogel backbone comprises a Matrix Metalloprotease (MMP) target substrate, or a portion thereof.

5. The system of claim 1, wherein the annealing agent comprises Eosin Y, a thiol group, or a combination thereof.

6. The system of claim 1, wherein the annealing agent comprises Factor XIII.

7. The system of claim 1, wherein a microgel particle of the plurality of microgel particles is substantially spherical in shape.

8. The system of claim 1, wherein at least one pore of the pores formed between the plurality of microgel particles comprises a diameter of about 2 to about 20 micrometers.

9. The system of claim 1, wherein at least one microgel particle of the plurality of microgel particles comprises a diameter that is about 50 to about 200 micrometers.

10. The system of claim 1, further comprising a light source configured to initiate the coupling of the one or more annealing components of the two or more microgel particles by the annealing agent.

11. The system of claim 1, wherein the plurality of microgel particles comprise a coefficient of variation less than 25% in size.

12. The system of claim 1, wherein one or more microgel particles of the plurality comprises an antigen, an adjuvant, or a combination thereof.

13. The system of claim 12, wherein the antigen, the adjuvant, or the combination thereof comprises an immunosuppressive agent.

14. The system of claim 12, wherein the antigen, the adjuvant, or the combination thereof is chemically bound to or loaded within the one or more microgel particles.

15. The system of claim 1, further comprising one or more living cells configured to be incorporated into the pores formed between the microgel particles.

16. The system of claim 1, wherein the plurality of microgel particles comprises a first type of microgel particle that is non-degradable and a second type of microgel particle that is degradable.

17. The system of claim 16, wherein the second type of microgel particle comprises an antigen, an adjuvant, or a combination thereof.

18. A pharmaceutical formulation comprising the system of claim 1, formulated for administration to a subject by injection.

* * * * *